(12) United States Patent
Itoh (10) Patent No.: US 7,687,033 B2
(45) Date of Patent: Mar. 30, 2010

(54) SPECIMEN ALIQUOTING/DISPENSING DEVICE INCORPORATED REFERENCE

(75) Inventor: Teruaki Itoh, Kumamoto (JP)

(73) Assignee: IDS Co., Ltd., Kumamoto-shi, Kumanoto (JP)

( * ) Notice: Subject to any disclaimer, the term of this patent is extended or adjusted under 35 U.S.C. 154(b) by 318 days.

(21) Appl. No.: 11/976,946

(22) Filed: Oct. 30, 2007

(65) Prior Publication Data

US 2008/0138249 A1 Jun. 12, 2008

(30) Foreign Application Priority Data

Dec. 7, 2006 (JP) ............... 2006-330972

(51) Int. Cl.
*B01L 3/02* (2006.01)
(52) U.S. Cl. .................... 422/100; 422/63; 422/64; 422/65; 73/863.32; 73/864; 73/864.01; 73/864.11; 73/864.17
(58) Field of Classification Search ............... 422/100, 422/63–65; 73/863.32, 864, 864.01, 864.11, 73/864.17
See application file for complete search history.

(56) References Cited

U.S. PATENT DOCUMENTS

| 5,336,467 | A | * | 8/1994 | Heidt et al. | .................... 422/64 |
| 5,479,969 | A | * | 1/1996 | Hardie et al. | ................ 141/130 |
| 6,045,759 | A | * | 4/2000 | Ford et al. | .................... 422/103 |
| 6,943,029 | B2 | * | 9/2005 | Copeland et al. | .............. 436/46 |
| 7,118,918 | B2 | * | 10/2006 | Copeland et al. | .............. 436/46 |
| 7,378,058 | B2 | * | 5/2008 | Lemme et al. | .............. 422/100 |
| 2002/0072122 | A1 | * | 6/2002 | Copeland et al. | .............. 436/46 |

FOREIGN PATENT DOCUMENTS

| JP | 6-323964 | 11/1994 |
| JP | 9-127130 | 5/1997 |
| JP | 2002-243750 | 8/2002 |
| JP | 2002-542017 | 12/2002 |
| JP | 2005-207850 | 8/2005 |
| JP | 2006-317330 | 11/2006 |

* cited by examiner

*Primary Examiner*—Brian R Gordon
(74) *Attorney, Agent, or Firm*—Nixon & Vanderhye P.C.

(57) ABSTRACT

A tip mounting position, an aliquoting position, a dispensing position, and a tip casting position are circumferentially arranged around a rotating shaft, and a plurality of aliquoting/dispensing mechanisms are circumferentially arranged corresponding to the plurality of operating positions around the rotating shaft. Each aliquoting/dispensing mechanism is provided with a nozzle lift mechanism and a nozzle mechanism that includes a nozzle lift mechanism and a nozzle portion. The rotating shaft is intermittently rotated to locate the aliquoting/dispensing mechanisms individually in the positions whereupon tip mounting, aliquoting, dispensing, and tip casting operations are performed continuously.

6 Claims, 5 Drawing Sheets

SPECIMEN ALIQUOTING/DISPENSING DEVICE INCORPORATED REFERENCE

CROSS-REFERENCE TO RELATED APPLICATIONS

This application is based upon and claims the benefit of priority from prior Japanese Patent Application No. 2006-330972, filed Dec. 7, 2006, the entire contents of which are incorporated herein by reference.

BACKGROUND OF THE INVENTION

1. Field of the Invention

The present invention relates to a specimen aliquoting/dispensing device for aliquoting a specimen, such as blood, from a test tube or some other specimen container that contains the specimen and dispensing the specimen into another specimen container.

2. Description of the Related Art

Pretreatment is performed before various blood tests, such as a biochemical analysis, are conducted. In this pretreatment, a test tube that contains a blood specimen is set in a centrifuge, whereby the specimen is centrifuged. Then, the blood serum in the test tube is aliquoted, and the aliquoted blood specimen is dispensed to a test container.

In general, the serum and clot of the centrifuged blood specimen in the test tube are generally separated in the test tube with use of a separating agent, such as silicone, so that an interface between the serum and clot portions can be clearly distinguished. Specifically, the centrifuged blood specimen is divided into three layers, the serum, separating agent, and clot, which are sequentially arranged from top to bottom in the test tube.

In aliquoting the serum in the test tube that is supported vertically, therefore, a tapered aliquoting/dispensing nozzle in the form of a hollow cone is inserted into the test tube, and only the serum is aliquoted by air suction by the nozzle. Then, the aliquoting/dispensing nozzle having aliquoted the serum is moved to another place, and the serum is dispensed to the test container.

Conventionally, an aliquoting/dispensing device for a specimen such as blood is known from Jpn. Pat. Appln. KOKAI Publication No. 6-323964. In this device, a head member is provided on the distal end portion of a sample supply/discharge pipe. The head member is provided with a balloon that is connected to a fluid supply/discharge pipe. This balloon is configured to be inflated or deflated with a fluid that is supplied or discharged through the fluid supply/discharge pipe.

The aliquoting/dispensing device is provided with an aliquoting/dispensing nozzle. A barrel portion is provided at the proximal end portion of the nozzle. If the fluid is supplied to the balloon through the fluid supply/discharge pipe with the head member including the balloon inserted in the barrel portion, the balloon is inflated and brought into close contact with the inner peripheral surface of the barrel portion of the nozzle. If the fluid in the balloon is discharged through the fluid supply/discharge pipe, on the other hand, the balloon is deflated and separated from the inner peripheral surface of the barrel portion of the nozzle. Thus, the head member and the aliquoting/dispensing nozzle can be attached to or detached from each other by inflating or deflating the balloon.

Further, a specimen aliquoting/dispensing device with an elastic bag is known from Jpn. Pat. Appln. KOKAI Publication No. 9-127130. The elastic bag is attached to the distal end portion of a body of an aliquoting/dispensing nozzle, and a fluid can be supplied to and discharged from it. If the fluid is supplied to the bag through a fluid supply/discharge pipe with the nozzle body including the bag inserted in a barrel portion at the proximal end portion of the nozzle, the bag is inflated and brought into close contact with the inner peripheral surface of the barrel portion of the nozzle. If the fluid in the bag is discharged through the fluid supply/discharge pipe, on the other hand, the bag is deflated and separated from the inner peripheral surface of the barrel portion of the nozzle. Thus, the nozzle body and the aliquoting/dispensing nozzle can be attached to or detached from each other by inflating or deflating the elastic bag.

In either of the devices described in Jpn. Pat. Appln. KOKAI Publications Nos. 6-323964 and 9-127130, however, the balloon is inflated or deflated by supplying or discharging the fluid so that it is pressed against or separated from the inner peripheral surface of the barrel portion of the aliquoting/dispensing nozzle, whereby the nozzle body and the nozzle are attached to or detached from each other. Since an additional device is needed to supply and discharge the fluid to and from the balloon, therefore, the construction of the nozzle device is complicated. Further, the balloon is expected to be inflated and deflated by the fluid supply and discharge, so that it should be formed thin-walled. Since the balloon is bound to rub repeatedly against the inner peripheral surface of the barrel portion of the nozzle, however, it is easily damaged by abrasion. Thus, the balloon requires troublesome maintenance work including frequency replacement.

Furthermore, the aliquoting/dispensing nozzle is attached to the nozzle body in a process for aliquoting the blood specimen in the test tube by means of the aliquoting/dispensing nozzle and dispensing the aliquoted specimen to another test container. Then, the blood specimen is aliquoted and dispensed by means of the nozzle. In doing this, however, the aliquoting/dispensing nozzle must be removed from the nozzle body and cast away every time the specimen is aliquoted and dispensed. This operation is so troublesome or complicated that the operating efficiency is poor, thus requiring automation.

BRIEF SUMMARY OF THE INVENTION

According to the present invention, a specimen aliquoting/dispensing device comprises: a device body; a drive mechanism attached to the device body; a conveyor attached to the device body and including a parent specimen lane for conveying a parent specimen and a child specimen lane for conveying a child specimen; a rotating shaft which is located projecting vertically from the device body and is intermittently rotated by the drive mechanism; a plurality of operating positions circumferentially arranged around the rotating shaft over the device body and including a tip mounting position, an aliquoting position, a dispensing position, and a tip casting position, the aliquoting position and the dispensing position being provided on the parent specimen lane and the child specimen lane, respectively; a plurality of aliquoting/dispensing mechanisms circumferentially arranged corresponding to the plurality of operating positions around the rotating shaft; nozzle lift mechanisms provided individually in the aliquoting/dispensing mechanisms; a nozzle mechanism including an aliquoting/dispensing pipe provided for up-and-down motion by the nozzle lift mechanism and a nozzle portion at a distal end portion thereof; an aliquoting/dispensing tip removably attached to the nozzle mechanism and configured to aliquot and dispense the specimens; an air supply/discharge mechanism which is provided in the aliquoting/dispensing mechanism and is configured to form a negative pressure for suction in the aliquoting/dispensing tip attached to the nozzle body in aliquoting the parent specimen situated in the aliquoting position by means of the aliquoting/dispensing tip and to form a positive pressure in the aliquoting/dispensing tip in dispensing the aliquoted specimen to the child specimen situated in the dispensing position; and means for intermittently rotating the rotating shaft to locate the aliquoting/dispensing mechanism in the tip mounting position, aliquoting position, dispensing position, and tip casting position and continuously performing tip mounting, aliquoting, dispensing, and tip casting operations therein.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will now be described with reference to the accompanying drawings.

Figures 1, 2:
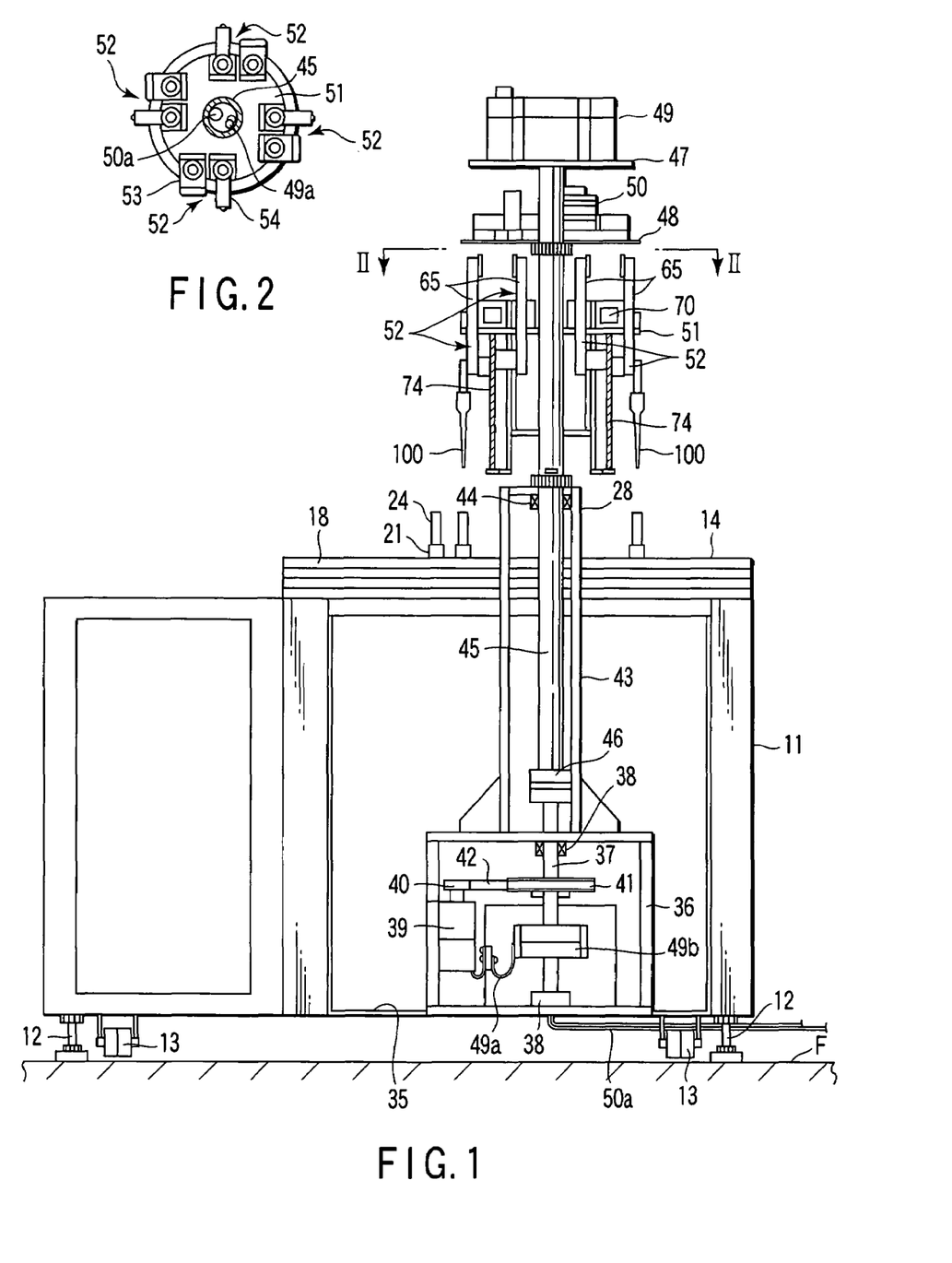
FIG. 1 is a longitudinal front view of a specimen aliquoting/dispensing device according to a first embodiment of the invention.
FIG. 2 is a sectional view of the device of the embodiment taken along line II-II of FIG. 1.
Figure 3:
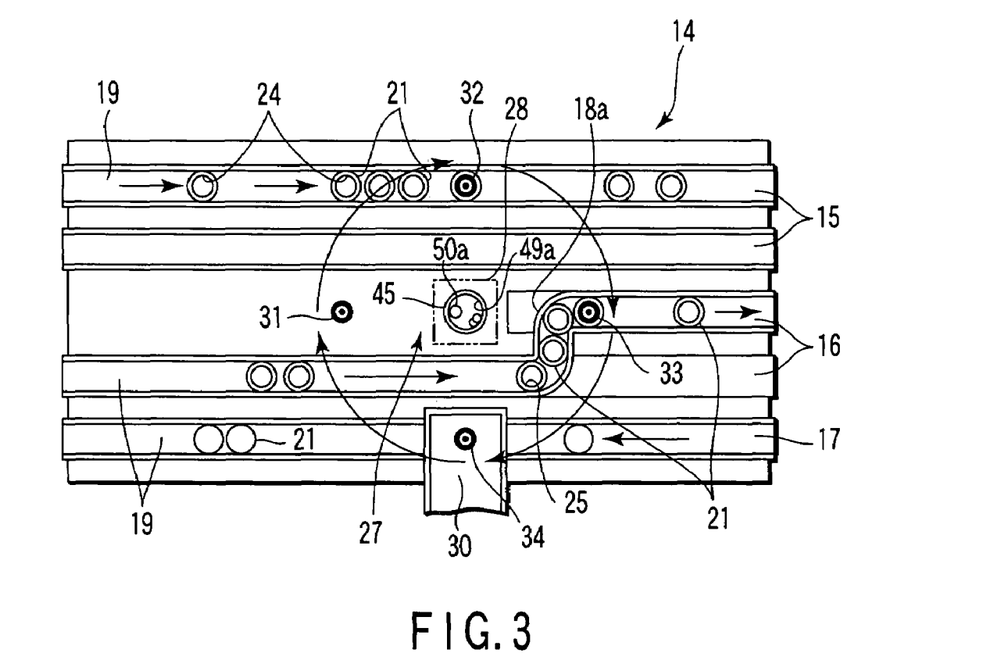
FIG. 3 is a schematic plan view of a conveyor of the embodiment.

As shown in FIGS. 1 and 2, a main body 11 of a specimen aliquoting/dispensing device is in the form of a rectangular box. Support legs 12 and casters 13 to be set on a floor surface F are attached to four corners of the bottom of the body 11. A conveyor 14 is provided on the top of the body 11. As shown in FIG. 3, the conveyor 14 includes two parent specimen lanes 15, two child specimen lanes 16, and one empty holder return lane 17 that are arranged parallel to one another and configured to run in the directions of arrows, individually. One of the two parent specimen lanes 15 is a bypass lane for specimens that are not to be aliquoted, while one of the two child specimen lanes 16 serves for change of course.

Figure 4:
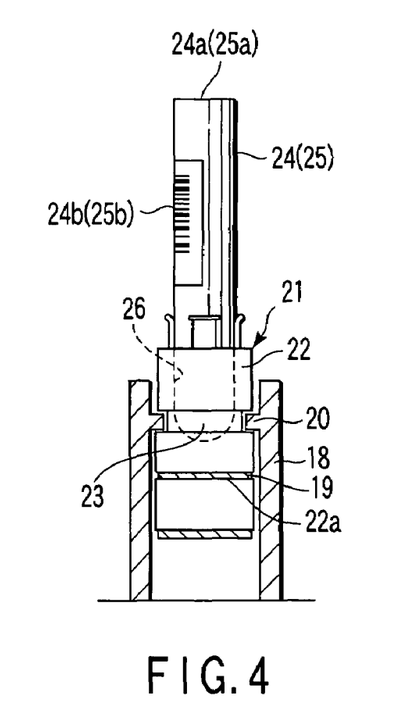
FIG. 4 is a sectional view of a rail portion.

The lanes 15, 16 and 17 have the same construction. As shown in FIG. 4, an endless conveyor belt 19 is provided on a bottom portion of a rail body 18 with a cross section shaped like a square U. Guide ridges 20 are arranged individually on two opposite side surfaces of the rail body 18 so as to extend in the longitudinal direction of the body 18. The rail body 18 is configured so that test tube holders 21 can be conveyed upright in a single file formation. Each test tube holder 21 has a cylindrical holder body 22 that is molded from a plastic material or the like. The holder body 22 is provided with a bottom portion 22a that is in contact with the conveyor belt 19. An annular groove 23 for engagement with the guide ridges 20 is formed on the outer peripheral portion of the holder body 22. The holder body 22 is kept upright as it is conveyed by the conveyor belt 19. It is provided with a fitting hole 26 in which a test tube 24 or a test container 25 is removably fitted. The test tube 24 serves as a test container 25 that can contain a parent specimen (unaliquoted specimen). The test container 25 can contain a child specimen (dispensed specimen).

The test tube 24 and the test container 25 are cylindrical tubes that are molded from a plastic material or the like. Their respective lower end portions can be removably supported in the fitting hole 26 of the holder body 22. Openings 24a and 25a are formed individually in their respective upper end portions. Further, identification labels 24b and 25b are stuck on the side surfaces of the test tube 24 and the test container 25, respectively.

As shown in FIG. 3, one of the two child specimen lanes 16 is bent in the middle toward the other child specimen lane 16, thereby forming a bent rail portion 18a for course change. Thus, the conveyor 14 is formed with a space portion 27 that adjoins the bent rail portion 18a. The space portion 27 is provided with a shaft supporting portion 28 for supporting a rotating shaft (mentioned later) on the main body 11 in an upright state. On the conveyor 14, moreover, a tip mounting position 31, aliquoting position 32, dispensing position 33, and tip casting position 34 are arranged at intervals of 90 degrees around the shaft supporting portion 28.

Thus, the tip mounting position 31 is located in the space portion 27, the aliquoting position 32 on one of the parent specimen lane 15, the dispensing position 33 on one of the child specimen lanes 16, and the tip casting position 34 opposite a tip casting chute 30 on the empty holder return lane 17.

The following is a description of the interior of the main body 11 of the specimen aliquoting/dispensing device. As shown in FIG. 1, a bottom plate 35 is disposed inside the body 11. A drive source box 36 is provided on the upper surface of the bottom plate 35. In the drive source box 36, a drive shaft 37 is located upright so as to face the shaft supporting portion 28. The upper and lower parts of the shaft 37 are rotatably supported by a bearing 38.

An electric motor 39 is fixed to an inner sidewall of the drive source box 36 with its rotating shaft upward. A driving pulley 40 is provided on the rotating shaft. A driven pulley 41 is fixed to the drive shaft 37. A belt 42 is passed around and between the pulleys 40 and 41 so that intermittent rotation of the motor 39 is transmitted to the drive shaft 37.

A support frame 43 is fixed upright on the top of the drive source box 36 and projects above the main body 11 through the space portion 27 of the conveyor 14. A rotating shaft 45 formed of a hollow pipe is rotatably supported on the support frame 43 by a bearing 44. The shaft 45 is connected directly to the drive shaft 37 by a coupling 46. Two horizontal support plates 47 and 48 are fixed to the upper end side of the shaft 45 so as to be spaced vertically. The support plates 47 and 48 are provided with a control section 49 and a base/piping equipment 50, respectively.

An electric wire 49a that is connected to an external power source is connected to the control section 49 through a slip ring 49b and the interior of the rotating shaft 45. An air pipe 50a that is connected to an external compressor is connected to the base/piping equipment 50 through the interior of the shaft 45.

A horizontal support member 51 is fixed to a substantially middle part of the rotating shaft 45 with respect to the vertical direction. The support member 51 is provided with four aliquoting/dispensing mechanisms 52, which are arranged at intervals of 90 degrees so as to face the tip mounting position 31, aliquoting position 32, dispensing position 33, and tip casting position 34 on the conveyor 14, individually.

Figure 5:
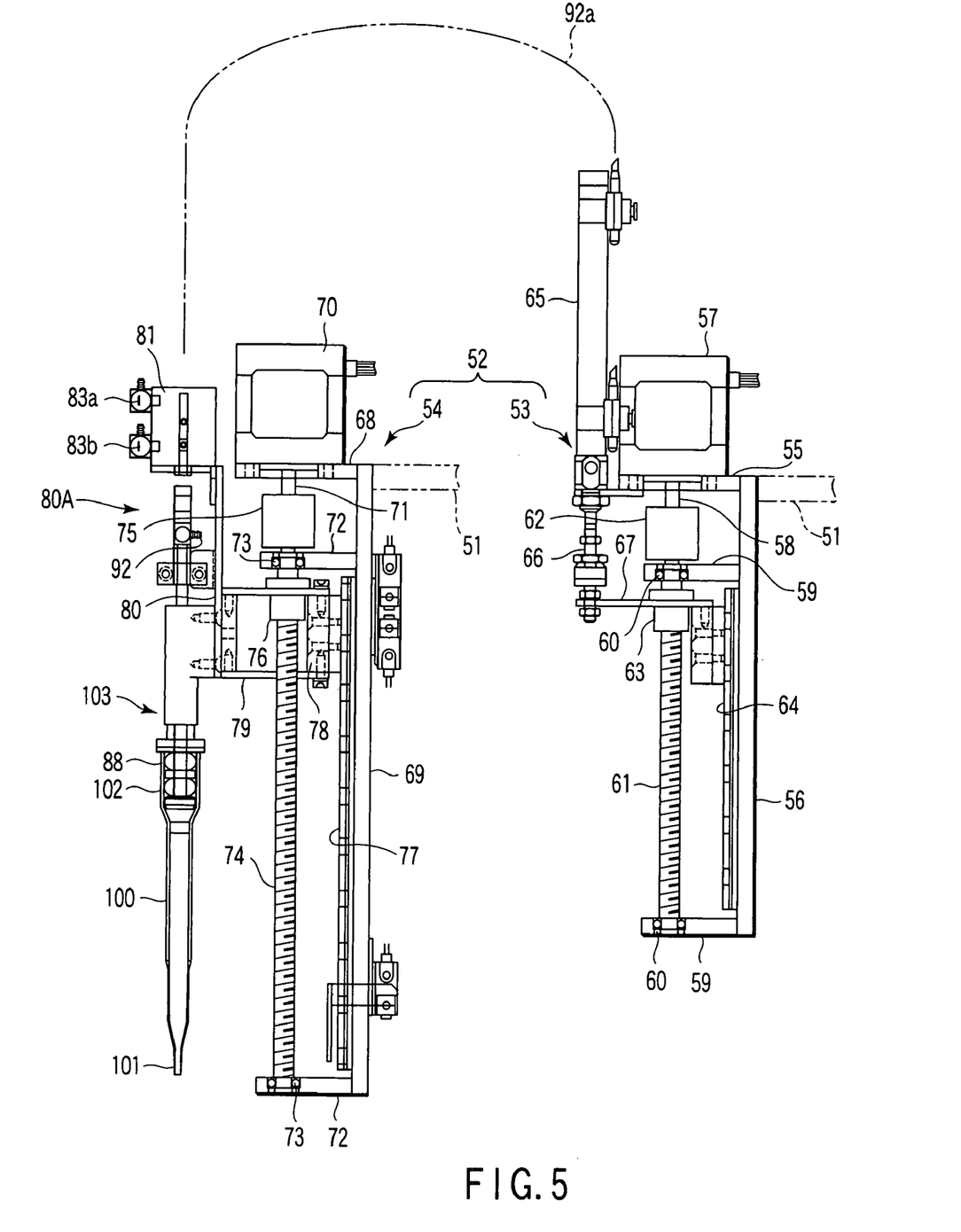
FIG. 5 is a side view showing a syringe mechanism and a nozzle lift mechanism of the embodiment.

Since the four aliquoting/dispensing mechanisms 52 have the same construction, only one of them will be described below. As shown in FIG. 5, the aliquoting/dispensing mechanism 52 is composed of a syringe mechanism 53 for use as air supply/discharge means and a nozzle lift mechanism 54. The syringe mechanism 53 will be described first. The support member 51 is fixedly fitted with a mounting frame 55 that projects horizontally. The mounting frame 55 is provided with a support frame 56 that projects vertically downward.

An electric motor 57 is fixed on the top of the mounting frame 55 with its rotating shaft 58 downward. The support frame 56 is fitted with brackets 59 that are spaced vertically. A ball screw 61 is vertically supported for rotation on the brackets 59 by bearings 60. The upper end portion of the screw 61 is connected to the shaft 58 of the motor 57 by a coupling 62. A nut 63 is threadedly fitted on the screw 61. The nut 63 is supported by a guide rail 64 on the support frame 56. As the ball screw 61 rotates forward or backward, the nut 63 ascends or descends.

A syringe 65 having a piston (not shown) therein is vertically fixed to the mounting frame 55. A piston rod 66 that is connected to the piston protrudes downward from the syringe 65. The rod 66 is connected to the nut 63 by a connecting member 67. As the nut 63 ascends or descends, therefore, the piston ascends or descends in the syringe 65 so that the syringe 65 can perform suction (aliquoting) and pressurization (dispensing), as mentioned later.

The following is a description of the nozzle lift mechanism 54. A horizontally projecting mounting frame 68 is fixed to the support member 51. It is provided with a mounting frame 69 that projects vertically downward.

An electric motor 70 is fixed on the top of the mounting frame 68 with its rotating shaft 71 downward. The support frame 69 is fitted with brackets 72 that are spaced vertically. A ball screw 74 is supported for rotation on the brackets 72 by bearings 73. The upper end portion of the screw 74 is connected to the shaft 71 of the motor 70 by a coupling 75. A nut 76 is threadedly fitted on the screw 74. The nut 76 is supported by a guide rail 77 on the support frame 69. As the ball screw 74 rotates forward or backward, the nut 76 ascends or descends.

A connecting member 78 is fixed to the nut 76, and a reinforcing member 79 that is supported by a guide rail 77 is fixed to the connecting member 78. A cylinder mounting member 80 is vertically fixed to the members 78 and 79. Thus, the cylinder mounting member 80 is configured to ascend and descend integrally with the nut 76.

Figure 6A:
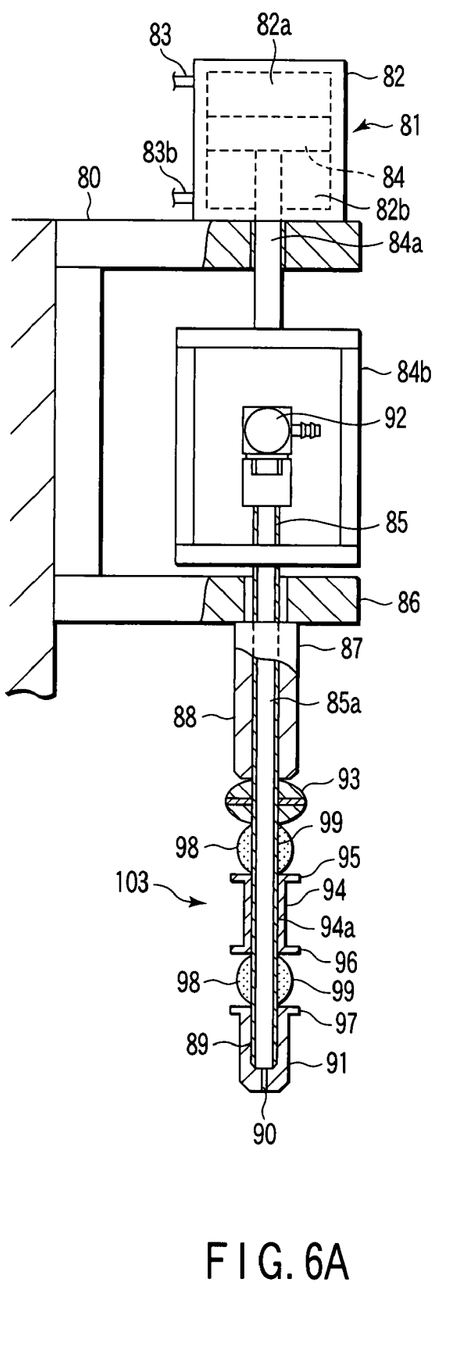
FIG. 6A is a longitudinal sectional side view showing an aliquoting/dispensing nozzle body of the embodiment with balls released from a compressive force.
Figure 6B:
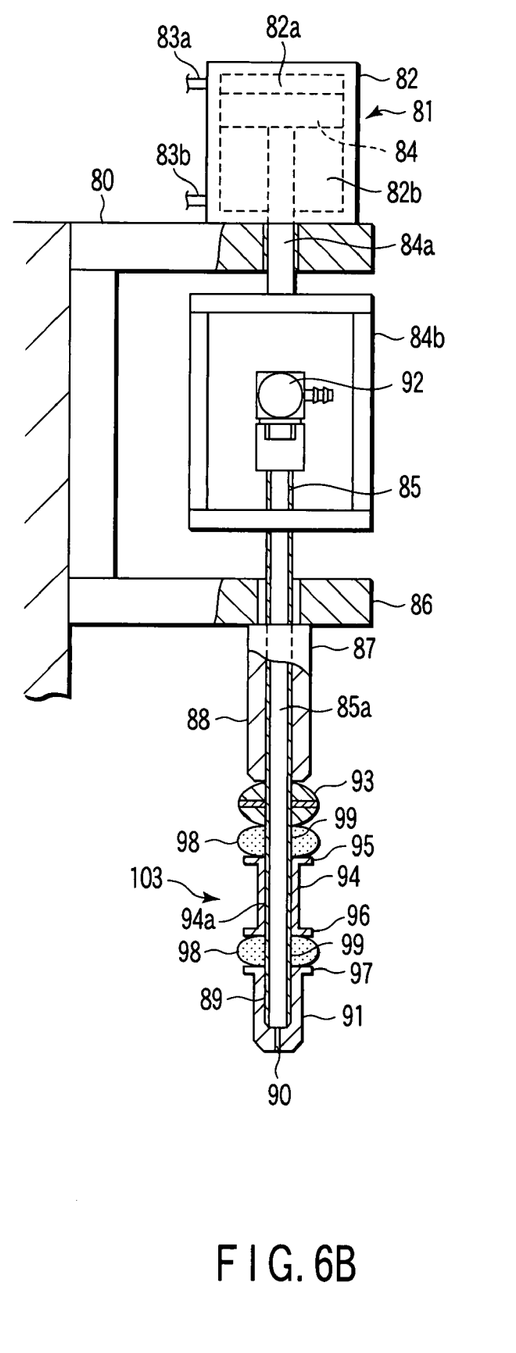
FIG. 6B is a longitudinal sectional side view showing the aliquoting/dispensing nozzle body of the embodiment with the balls compressed.
Figure 7:
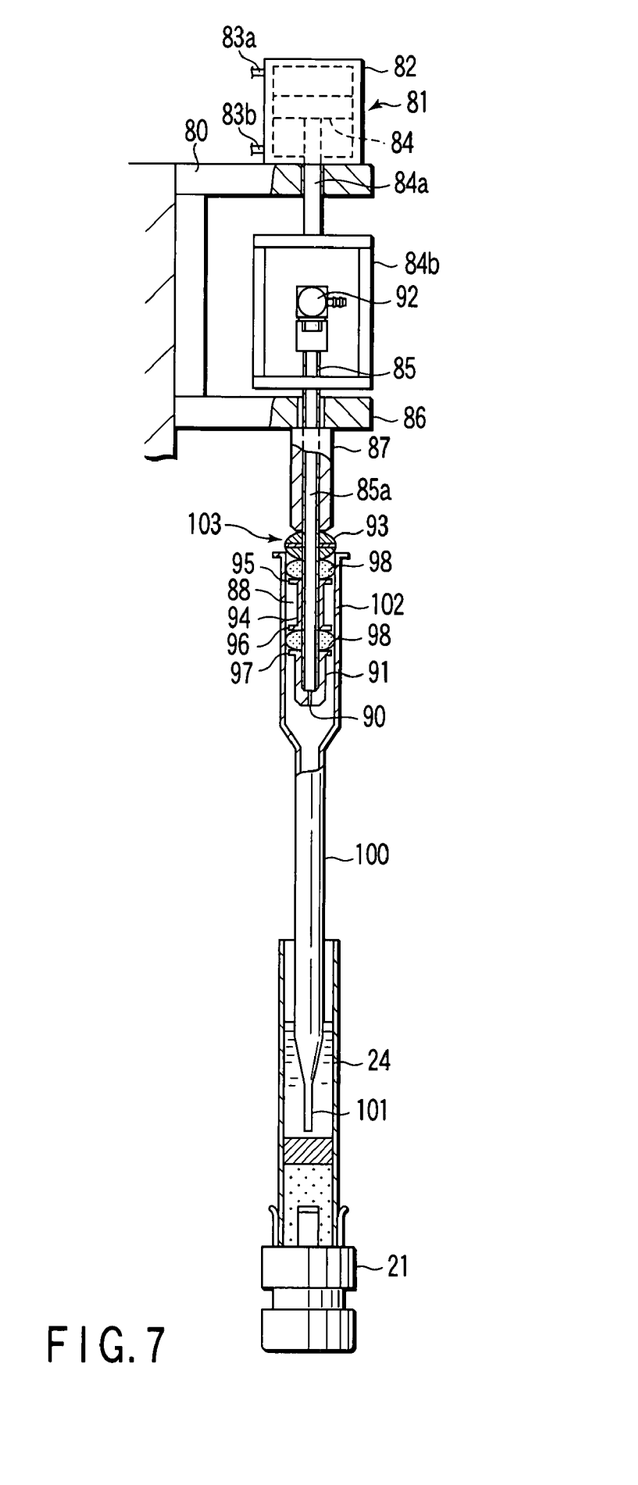
FIG. 7 is a longitudinal sectional side view showing the embodiment with an aliquoting/dispensing tip attached to the nozzle body.

The cylinder mounting member 80 is mounted with a ball compression mechanism 80A, which is constructed in the manner shown in FIGS. 6A, 6B and 7. Specifically, an air cylinder 81 is located vertically. A cylinder portion 82 of the air cylinder 81 is divided into upper and lower chambers 82a and 82b, which are connected with air supply/discharge pipes 83a and 83b, respectively. A piston 84 is moved up and down by air that is supplied and discharged through the pipes 83a and 83b. The air supply/discharge pipes 83a and 83b are connected to the base/piping equipment 50 by piping (not shown).

A plunger 84a is connected to the piston 84, and a lift frame 84b is provided on the distal end portion of the plunger 84a. An aliquoting/dispensing pipe 85 is connected to the lift frame 84b. It is supported for up-and-down motion by a guide pipe 87 that is fixed to a cylinder mounting member 86. The pipe 85 is configured to be moved up and down by the air cylinder 81. A nozzle mechanism 103 is provided on the lower end portion of the aliquoting/dispensing pipe 85 that projects downward from the guide pipe 87.

Specifically, a mounting portion 89 formed of a screw is provided on the distal end portion of the aliquoting/dispensing pipe 85, and a nozzle portion 91 having a nozzle hole 90 in its distal end is fixed to the mounting portion 89. The nozzle hole 90 of the nozzle portion 91 communicates with a pipe joint 92 through a passage 85a of the aliquoting/dispensing pipe 85. The pipe joint 92 is connected to the syringe 65 by a tube 92a so that the syringe 65 can aliquot and dispense a specimen such as blood.

Further, an upper fixed flange portion 93, through which the aliquoting/dispensing pipe 85 is movable in its axial direction, is provided on the lower end portion of the guide pipe 87. The flange portion 93 is underlain by a moving cylinder 94 that has a through hole 94a through which the aliquoting/dispensing pipe 85 is movable in the axial direction. Movable flange portions 95 and 96 are formed integrally on the upper and lower end portions of the moving cylinder 94. The upper movable flange portion 95 of the cylinder 94 is opposed to and spaced from the upper fixed flange portion 93, while the lower movable flange portion 96 is opposed to and spaced from the lower fixed flange portion 97 that is integral with the nozzle portion 91.

Thus, gap portions are provided individually between the upper fixed flange portion 93 and the movable flange portion 95 and between the lower fixed flange portion 97 and the movable flange portion 96. Elastically deformable silicone balls 98 are held individually in these gap portions. Each silicone ball 98 is a solid sphere that has a through hole 99 through which the aliquoting/dispensing pipe 85 is movable in the axial direction. When the balls 98 are compressed vertically, they are elastically deformed so that their diameters become larger than the outside diameters of the movable flange portions 95 and 96 and the lower fixed flange portion 97. When the compressive force is removed, the diameters of the balls 98 become smaller than the outside diameters of the movable flange portions 95 and 96 and the lower fixed flange portion 97.

As shown in FIG. 7, moreover, an aliquoting/dispensing tip 100 is a cylindrical body of transparent plastic or glass, which can be attached to and detached from a nozzle body 88 and store a specimen such as blood. The tip 100 serves to aliquot and dispense the specimen. It is provided with a tapered portion 101 at its distal end portion and a barrel portion 102 at its proximal end portion. The inside diameter of the barrel portion 102 is larger than the respective outside diameters of the movable flange portions 95 and 96 and the lower fixed flange portion 97 of the nozzle body 88 and the silicone balls 98. Thus, the flange portions 95, 96 and 97 including the nozzle portion 91 and the balls 98 can be inserted into the barrel portion 102.

The following is a description of the operation of the specimen aliquoting/dispensing device constructed in this manner.

Each test tube 24 that is stored with the specimen is fed onto the parent specimen lane 15 of the conveyor 14 in a manner such that it is held in the test tube holder 21. Then, as the conveyor belt 19 travels, the test tube 24 is conveyed in the direction of the arrow. When it reaches the aliquoting position 32, the test tube 24 is temporarily stopped by stopper means (not shown). In this state, the nozzle body 88 of the nozzle lift mechanism 54 is temporarily stopped facing the tip mounting position 31, and the aliquoting/dispensing tip 100 is attached to the nozzle body 88.

The following is a description of the way the aliquoting/dispensing tip 100 is attached to the nozzle body 88. When the piston 84 of the air cylinder 81 is in a neutral state, the aliquoting/dispensing pipe 85 projects downward. In this state, no pressure acts on the silicone balls 98 between the upper fixed flange portion 93 and the movable flange portion 95 and between the lower fixed flange portion 97 and the movable flange portion 96, so that the balls 98 are spherical. When the motor 70 is driven in this state, the ball screw 74 rotates, whereupon the nut 76 is guided by the guide rail 77 to lower the cylinder mounting member 80.

The air cylinder 81 on the cylinder mounting member 80 and the nozzle body 88 descend. When this is done, the aliquoting/dispensing tip 100 is positioned upright with its barrel portion 102 upward, so that the nozzle body 88 can be inserted into the barrel portion 102. In other words, the movable flange portions 95 and 96 and the lower fixed flange portion 97 including the nozzle portion 91 and the silicone balls 98 can be inserted into the barrel portion 102. When air is then fed through the air supply/discharge pipe 83b into the lower chamber 82b of the cylinder portion 82, it is discharged through the air supply/discharge pipe 83a, whereupon the piston 84 ascends in the cylinder portion 82.

Since the aliquoting/dispensing pipe 85 is raised by the lift frame 84b as the piston 84 ascends, the nozzle portion 91 also ascends. Accordingly, the space between the upper and lower fixed flange portions 93 and 97 narrows, the upper fixed flange portion 93 and the movable flange portion 95 approach each other, and the lower fixed flange portion 97 and the movable flange portion 96 approach each other. Thus, the silicone balls 98 are compressed and elastically deformed so that their diameters become larger than the outside diameters of the movable flange portions 95 and 96 and the lower fixed flange portion 97.

When the silicone balls 98 are elastically deformed so that their diameters increase, they come into close contact with the inner peripheral surface of the barrel portion 102 of the aliquoting/dispensing tip 100, so that the nozzle body 88 and the tip 100 are connected to each other in an airtight manner, as shown in FIG. 7.

When the electric motor 39 in the main body 11 is driven in this state, the driving pulley 40 rotates, and the driven pulley 41 is rotated by the belt 42. The rotation of the driven pulley 41 is transmitted through the drive shaft 37 to the rotating shaft 45, whereupon the mechanism support member 51 integrally rotates by 90 degrees. Thereupon, the aliquoting/dispensing tip 100 that is attached to the nozzle body 88 in the tip mounting position 31 moves to and faces the aliquoting position 32 on the conveyor 14.

When the electric motor 70 of the nozzle lift mechanism 54 is driven again in this state, the ball screw 74 rotates, whereupon the nut 76 descends guided by the guide rail 77 and the cylinder mounting member 80 also descends. Then, the air cylinder 81 on the mounting member 80 and the nozzle body 88 descend, and the tapered portion 101 of the aliquoting/dispensing tip 100 is inserted into the test tube 24 that is supported by the test tube holder 21.

When the electric motor 57 of the syringe mechanism 53 is driven in this state, the ball screw 61 rotates, whereupon the nut 63 descends guided by the guide rail 64 and the piston rod 66 also descends. When the syringe 65 then performs suction, the internal pressure of the aliquoting/dispensing tip 100 is reduced to a negative pressure by the aliquoting/dispensing pipe 85. Thereupon, blood serum in the test tube 24 can be sucked in and aliquoted into the aliquoting/dispensing tip 100.

When the aliquoting process is completed, the electric motor 70 rotates reversely. As the motor 70 rotates in this manner, the ball screw 74 rotates and the nut 76 is guided by the guide rail 77 to raise the cylinder mounting member 80.

When the nozzle body 88 and the aliquoting/dispensing tip 100 ascend integrally with each other, the tip 100 that is stored with the aliquoted serum gets out of the test tube 24.

When the electric motor 39 in the main body 11 is driven again, the driving pulley 40 rotates, and the driven pulley 41 is rotated by the belt 42. The rotation of the driven pulley 41 is transmitted through the drive shaft 37 to the rotating shaft 45, whereupon the nozzle support member 51 integrally rotates by 90 degrees. Thereupon, the serum is aliquoted in the aliquoting position 32, and the aliquoting/dispensing tip 100 that is attached to the nozzle body 88 faces the dispensing position 33 on the conveyor 14. When this is done, the test container 25 for accommodating the child specimen is held on standby in the dispensing position 33 on the child specimen lane 16 in a manner such that it is supported by the test tube holder 21. Thus, the aliquoting/dispensing tip 100 that is attached to the nozzle body 88 faces the dispensing position 33 on the conveyor 14.

When the electric motor 70 is then driven again, the ball screw 74 rotates, whereupon the nut 76 is guided by the guide rail 77 to lower the cylinder mounting member 80. Then, the air cylinder 81 on the mounting member 80 and the nozzle body 88 descend, and the tapered portion 101 of the aliquoting/dispensing tip 100 is inserted into the test container 25.

When the electric motor 57 of the syringe mechanism 53 rotates reversely in this state, the ball screw 61 rotates, whereupon the nut 63 ascends guided by the guide rail 64 and the piston rod 66 also ascends. When the syringe 65 then performs exhaust, the internal pressure of the aliquoting/dispensing tip 100 is increased to a positive pressure by the aliquoting/dispensing pipe 85. Thereupon, the serum in the tip 100 can be dispensed to the test container 25.

When the dispensing process is finished, the electric motor 70 rotates reversely. As the motor 70 rotates in this manner, the ball screw 74 rotates and the nut 76 is guided by the guide rail 77 to raise the cylinder mounting member 80. When the nozzle body 88 and the aliquoting/dispensing tip 100 ascend integrally with each other, the empty tip 100 having undergone the dispensing operation gets out of the test container 25.

When the electric motor 39 in the main body 11 is driven again, the driving pulley 40 rotates, and the driven pulley 41 is rotated by the belt 42. The rotation of the driven pulley 41 is transmitted through the drive shaft 37 to the rotating shaft 45, whereupon the nozzle support member 51 integrally rotates by 90 degrees. Thereupon, the aliquoting/dispensing tip 100 having dispensed the serum in the dispensing position 33 faces the tip casting position 34 on the conveyor 14.

When the aliquoting/dispensing operation is finished in this manner, air is fed through the air supply/discharge pipe 83a into the upper chamber 82a of the cylinder portion 82 and discharged through the air supply/discharge pipe 83b, whereupon the piston 84 descends in the cylinder portion 82. Thus, the nozzle portion 91 on the distal end portion of the aliquoting/dispensing pipe 85 that is integral with the piston 84 descends. Then, the space between the upper and lower fixed flange portions 93 and 97 widens, and the compressive force on the silicone balls 98 between the flange portions 93 and 97 is removed. Thereupon, the balls 98 become smaller in diameter than the movable flange portions 95 and 96 and the lower fixed flange portion 97.

When the silicone balls 98 are reduced in diameter, they leave the inner peripheral surface of the barrel portion 102 of the aliquoting/dispensing tip 100, so that the nozzle body 88 and the tip 100 are disconnected from each other. Thereupon, the tip 100 is separated from the nozzle portion 91 and dropped into a tip recovery box through the tip casting chute 30.

When the tip casting process is completed, the electric motor 39 in the body 11 is driven again to rotate the driving pulley 40, and the driven pulley 41 is rotated by the belt 42. The rotation of the driven pulley 41 is transmitted through the drive shaft 37 to the rotating shaft 45, whereupon the nozzle support member 51 integrally rotates by 90 degrees. Thereupon, the nozzle portion 91 having cast the aliquoting/dispensing tip 100 in the tip casting position 34 returns to the tip mounting position 31, whereupon one cycle is completed. Then, in the tip mounting position 31, the aliquoting/dispensing tip 100 is attached again to the nozzle body 88. Aliquoting/dispensing processes for specimens such as blood can be continuously performed by repeating these operations.

While the aliquoting/dispensing tip 100 is being attached to the nozzle body 88 in the tip mounting position 31, moreover, the syringe mechanism 53 and the nozzle lift mechanism 54 are driven independently. Further, the aliquoting and dispensing operations are performed in the aliquoting position 32 and the dispensing position 33, respectively. Thus, the operating efficiency can be improved.

According to the embodiment described above, the four positions, that is, the tip mounting position 31, aliquoting position 32, dispensing position 33, and tip casting position 34, are arranged at intervals of 90 degrees. Alternatively, eight similar positions may be arranged at intervals of 45 degrees without being limited in number or restricted by the configuration.

According to the embodiment described herein, the aliquoting/dispensing pipe is connected directly to the cylinder so that it can be raised and lowered by the cylinder to compress and release the silicone balls. However, the cylinder may be replaced with an actuator, such as a motor-driven rack-and-pinion mechanism or a solenoid.

Although the two silicone balls are compressed and brought into close contact with the inner peripheral surface of the tube portion of the aliquoting/dispensing tip, moreover, they may be replaced with balls of any other plastic material than silicone, and their number is not limited to two.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A specimen aliquoting/dispensing device comprising:
   a device body;
   a drive mechanism attached to the device body;
   a conveyor attached to the device body and including a parent specimen lane for conveying a parent specimen and a child specimen lane for conveying a child specimen;
   a rotating shaft which is located projecting vertically from the device body and is intermittently rotated by the drive mechanism;
   said rotating shaft having a plurality of operating positions which are provided circumferentially around the rotating shaft over the device body and which include a tip mounting position, an aliquoting position, a dispensing position, and a tip casting position,
   the aliquoting position and the dispensing position being provided on the parent specimen lane and the child specimen lane, respectively;
   a plurality of aliquoting/dispensing mechanisms circumferentially arranged corresponding to the plurality of operating positions around the rotating shaft; and
   means for intermittently rotating the rotating shaft to locate the aliquoting/dispensing mechanism in the tip mounting position, aliquoting position, dispensing position, and tip casting position and continuously performing tip mounting, aliquoting, dispensing, and tip casting operations therein
   wherein each aliquoting/dispensing mechanism comprises a nozzle lift mechanism;
   each nozzle mechanism including an aliquoting/dispensing pipe provided for up-and-down motion by the nozzle lift mechanism and a nozzle portion at a distal end portion thereof;
   an aliquoting/dispensing tip removably attached to the nozzle mechanism and configured to aliquot and dispense the specimens;
   an air supply/discharge mechanism which is provided in the aliquoting/dispensing mechanism and is configured to form a negative pressure for suction in the aliquoting/dispensing tip attached to the nozzle body in aliquoting the parent specimen situated in the aliquoting position by means of the aliquoting/dispensing tip and to form a positive pressure in the aliquoting/dispensing tip in dispensing the aliquoted specimen to the child specimen situated in the dispensing position.

2. A specimen aliquoting/dispensing device according to claim 1, wherein the tip mounting position, aliquoting position, dispensing position, and tip casting position are arranged at intervals of 90 degrees around the rotating shaft, and four said aliquoting/dispensing mechanisms are arranged corresponding to the four positions, individually.

3. A specimen aliquoting/dispensing device according to claim 1, wherein the nozzle mechanism is independently raised and lowered by the nozzle lift mechanism and performs the tip mounting, aliquoting, dispensing, and tip casting operations in the tip mounting position, aliquoting position, dispensing position, and tip casting position, respectively.

4. A specimen aliquoting/dispensing device according to claim 1, wherein the nozzle lift mechanism is composed of an electric motor, a ball screw configured to be driven by the motor, a nut threadedly fitted on the screw, and a guide rail which linearly guides the nut in ascending and descending directions.

5. A specimen aliquoting/dispensing device according to claim 1, wherein the nozzle lift mechanism is composed of an electric motor, a ball screw configured to be driven by the motor, a nut threadedly fitted on the screw, and a syringe including a piston rod connected to the nut.

6. A specimen aliquoting/dispensing device according to claim 1, wherein the nozzle mechanism is composed of a nozzle body, a ball attached to the nozzle body, inserted in the aliquoting/dispensing tip, and configured to be elastically deformed in a diameter-increasing direction such as to project from an outer peripheral surface of the nozzle body to be in close contact with an inner peripheral surface of the aliquoting/dispensing tip, thereby mounting the tip in position, when compressed, and a ball compression mechanism configured to compress and elastically deform the balls in the diameter-increasing direction when the nozzle body including the ball is inserted in the aliquoting/dispensing tip in mounting the tip and to release the ball from a compressive force so that the ball is reduced in diameter and separated from the inner peripheral surface of tip in removing the tip.

* * * * *